United States Patent
Sassmannshaus et al.

(10) Patent No.: US 11,576,357 B2
(45) Date of Patent: Feb. 14, 2023

(54) METHODS AND SYSTEMS FOR INSECT FARMING

(71) Applicant: Ovipost, Inc., San Francisco, CA (US)

(72) Inventors: Brendon Sassmannshaus, San Francisco, CA (US); James Daniel Ricci, San Francisco, CA (US); Trina Chiasson, San Francisco, CA (US); Scott Campbell, Halifax (CA); Jane Kramer Ouillette, Morrill, ME (US); Colin Terry Gardiner, Bedford (CA); Megan Renee Clarke, Victoria (CA)

(73) Assignee: Ovipost, Inc., San Francisco, CA (US)

( * ) Notice: Subject to any disclaimer, the term of this patent is extended or adjusted under 35 U.S.C. 154(b) by 190 days.

(21) Appl. No.: 16/356,857

(22) Filed: Mar. 18, 2019

(65) Prior Publication Data

US 2019/0281799 A1     Sep. 19, 2019

Related U.S. Application Data

(60) Provisional application No. 62/644,437, filed on Mar. 17, 2018.

(51) Int. Cl.
*A01K 67/033* (2006.01)
*A01K 29/00* (2006.01)
(Continued)

(52) U.S. Cl.
CPC .......... *A01K 67/033* (2013.01); *A01K 29/005* (2013.01); *A01M 1/023* (2013.01); *A01M 1/04* (2013.01); *A01K 2227/706* (2013.01)

(58) Field of Classification Search
CPC ............... A01K 67/033; A01K 29/005; A01K 2227/706; A01K 29/00; A01M 1/023; A01M 1/02; A01M 1/04
(Continued)

(56) References Cited

U.S. PATENT DOCUMENTS

| 3,086,497 A | * | 4/1963 | Novello | ................. | A01K 61/59 |
| | | | | | 119/206 |
| 3,678,899 A | * | 7/1972 | Lovitz | .................... | A01K 61/85 |
| | | | | | 119/206 |

(Continued)

FOREIGN PATENT DOCUMENTS

KR         102347919 B1 *  1/2022

*Primary Examiner* — David J Parsley
*Assistant Examiner* — Morgan T Jordan
(74) *Attorney, Agent, or Firm* — Cognition IP, P.C.; Edward Steakley (57) ABSTRACT

Methods and systems are provided to insect harvesting. The system may include a tank for holding or growing live insects or both. The tank has an opening on a side portion of the tank, and the opening is positioned higher than a bottom portion of the tank. A negative stimulus device for repelling live insects toward a first direction or point towards the opening on the side portion of the tank is provided. A positive stimulus device is provided, situated at the opening of the tank. A product box for receiving live insects has an opening for receiving the live insects. A slide is coupled with the opening of the product box. In an operative position, the tank is positioned such that the live insects leaving the opening of the tank move down the slide to the opening of the product box.

10 Claims, 7 Drawing Sheets

(51) Int. Cl.
*A01M 1/04* (2006.01)
*A01M 1/02* (2006.01)

(58) Field of Classification Search
USPC .......................................................... 119/6.5
See application file for complete search history.

(56) References Cited

U.S. PATENT DOCUMENTS

| | | | | |
|---|---|---|---|---|
| 3,893,420 | A * | 7/1975 | Andreev | A01K 67/033 119/6.6 |
| 4,557,069 | A * | 12/1985 | Caldwell | A01M 1/02 43/107 |
| 5,423,291 | A * | 6/1995 | Daugherty | A01K 39/012 119/52.2 |
| 6,644,242 | B2 * | 11/2003 | Yamada | A01K 61/17 119/206 |
| 8,327,797 | B1 * | 12/2012 | Morales-Ramos | A01K 67/033 119/6.5 |
| 10,051,845 | B1 * | 8/2018 | Massaro | A01K 67/033 |
| 10,912,288 | B1 * | 2/2021 | Hall | A01K 29/00 |
| 2012/0145081 | A1 * | 6/2012 | Acar | A01K 67/033 119/6.5 |
| 2013/0081572 | A1 * | 4/2013 | Chen | A01K 67/033 119/6.5 |
| 2014/0020630 | A1 * | 1/2014 | Courtright | A01K 67/033 119/6.6 |
| 2015/0296760 | A1 * | 10/2015 | Perednia | A01K 67/033 119/6.5 |
| 2017/0042131 | A1 * | 2/2017 | Unger | A01K 67/033 |
| 2017/0265443 | A1 * | 9/2017 | Winston, III | B65D 85/50 |
| 2018/0007875 | A1 * | 1/2018 | Hall | A01K 7/02 |
| 2019/0387704 | A1 * | 12/2019 | Hall | A01K 67/033 |
| 2020/0359608 | A1 * | 11/2020 | Du | G06M 7/00 |
| 2021/0045368 | A1 * | 2/2021 | Jacobs | B65G 27/20 |

* cited by examiner

METHODS AND SYSTEMS FOR INSECT FARMING

CROSS-REFERENCE TO RELATED APPLICATIONS

This application claims the benefit of U.S. Provisional Patent Application No. 62/644,437, filed Mar. 17, 2018, which is/are all hereby incorporated by reference in their entirety.

FIELD OF THE INVENTION

The present invention relates to methods of farming and harvesting of insects, including but not limited to crickets

BACKGROUND

Considerable resources are required to raise and produce traditional animal food protein sources like cattle and poultry. For example, raising cattle requires a large amount of feed, water, fertilizer, land, and machinery. In contrast, it is considerably less resource intensive to raise insects as food sources than animal protein. Insects are eaten in many cultures. Since mass commercial production of insects for food is a relatively new practice, there are many unsolved problems.

One problem in the art relates to harborages used in insect farming. A harborage is any object that insects may hide behind. As it relates to insect farming, harborages are used as living environments of the insects while they grow to maturity. Current harborages used in insect farming are typically ad hoc objects made of paper fiber, such as egg cartons, and are not specifically designed for use as a harborage. In the high humidity environments of insect farms, or where there are other sources of moisture, these types of harborages are prone to quickly mold, creating an undesirable environment for raising insects. When the paper fiber harborages mold, they cannot be sanitized and cleaned.

Another problem in the art relates to absorptive materials used to water crickets. In current insect farming techniques, water may be provided to the insects through sponges or other absorptive material. In high temperature and humidity, or where there are other sources of moisture, these absorptive materials are subject to bacteria and fungus growth that quickly contaminate the entire surface. The breeding of fungus and bacteria fouls the water meant for insect consumption. As this is undesirable and detrimental to raising the insects, these absorptive materials must be frequently replaced by human workers.

Another problem in the art relates to disease outbreaks in populations of farmed insects. In high temperature and humidity environments, or where there are other sources of moisture, viral zoonotic disease outbreaks may occur. These outbreaks may decimate populations of insects, and thus, is undesirable in the farming of insects. Currently in insect farming operations, a 10% bleach solution is used to wipe down environments where zoonotic diseases have broken out. Farm workers must first remove or harvest all of the insects prior to cleaning, ending the breeding cycle and causing monetary damages to the farming operation. This process can be difficult, and if the bleach solution is not applied thoroughly and diligently, the zoonotic diseases may not be eradicated. Another technique of dealing with zoonotic disease is to abandon the original location of the outbreak and move the operation to a new location, and to return after one or two years. This process is costly, and the abandoned facility is only sometimes found to be uninfected.

Another problem in the art relates to determining when to perform certain actions when farming insects such as changing the nutrition for the insects, harvesting insects, setting out egg trays, and so on. In current insect farming operations involving sound-producing insects, insect farmers spend years gaining experience and tuning their ear to listen for audible signs that the insects are in particular developmental stages or are experiencing conditions that are disturbing their development. While sufficient for individual, smaller farming operations, this ad hoc human system is non-trainable, non-quantifiable, and variable across different insect farms.

Another problem in the art relates to the fouling of absorptive materials used for watering insects. In current insect farming operations, insects are often fed through wet, absorptive materials. These materials may experience fouling due to fecal matter and other bio contaminants on the surface of the absorptive material. In order to reduce the loss of insects due to disease spread through the fouled absorptive materials, farm workers wash and replace the water feeders very often. Some farming operations will also have periodic maintenance performed where fecal matter is scooped off of the absorptive material. This practice is both labor intensive and suboptimal as it does not prevent the feces from gathering on the absorptive material. It merely limits the time the feces are in contact with the absorptive material.

Another problem in the art relates to current insect egg trays being of unknown quantity. It would be desirable for insect farming operations to have accurate insect egg counts for planning and breeding purposes. Often, insect farmers do not have enough eggs to replenish their insect population, which is detrimental to keeping the farm operations at full capacity. Insect harvest cycles may be less than 2 months, so replenishing a partially full stock may take 4 to 6 months. Some farming operations have agreements with other farms to exchange trays of eggs. These trays are large pie tins lined with peat moss, and the eggs contained therein are of unknown quantity. Each farming operation must then hatch the eggs, measure and count them, distribute them into tanks, and raise them. The current method for counting the insects may involve dumping them into graduated cylinders and then dumping them into the tanks. This process results in loss of insects as many may suffocate and is also labor intensive.

Another problem in the art relates to separating live and dead insects for harvesting. At a certain maturation stage, insects in farming operations may be harvested for food production. The harvest operation is both labor and time intensive as the tanks of insects contain harvestable living adult insects, dead insects, feces, insect exoskeletons, and miscellaneous debris that must be separated. The currently practiced technique of separating the harvestable adult insects from the other undesirable remnants is to place cardboard into the tanks of insects and allow the living insects to climb on to and then to shake the cardboard into another vessel. This technique must be performed multiple times to capture all the living insects.

Another problem in the art relates to the need to replace and refill the water in insect tanks. Current insect farming operations distribute water to insects via watering rings with wet absorptive materials. The watering rings are attached to hoppers of water that need to be individually replaced with full containers periodically. Insect farmers may change the water manually, including on weekend days. This is currently a time intensive practice.

SUMMARY OF THE INVENTION

Embodiments relate to improving the efficiency of insect farming.

One embodiment relates to a washable insect harborage.

One embodiment relates to disinfecting a water supply for insects using ozone. An ozonator may infuse water with ozone that is presented to insects using a water presentation device.

One embodiment relates to treating insects with antivirals or antibiotics. A zoonotic infection may be identified, and an appropriate antiviral or antibiotic may be selected and administered.

One embodiment relates to processing chirp information from insects to determine the appropriate time perform certain farm actions.

One embodiment relates to placing an absorptive watering device on a ceiling, wall, overhang, or tilted mount by using gravity to remove disease spreading pathogens.

One embodiment relates to an egg pod with a counted number of insect eggs.

One embodiment relates to an automated insect harvested that automatically harvests insects.

One embodiment relates to an automated insect water system that delivers water to insect tanks in an automated manner.

Another embodiment relates to a system for harvesting insects, the system including a tank for holding or growing insects or both; a negative stimulus device for moving live insects toward a direction or point; and a positive stimulus device for attracting live insects toward a second direction or point, wherein the system separates live insects from dead insects. The system may also include: a one-way valve or device that inhibits an insect from returning to the tank, a slide or device that directs an insect toward a destination; wherein the first direction or point is the same as the second direction or point; a camera for observing insects, a (video) camera for counting insects, a computer for recording data, a destination box for capturing live insects; a sensor or scale for counting, weighing or quantifying live insects in a destination box; wherein the destination box is a product box, or the negative stimulus device creating one or more of the following: light, sound, vibration.

Another embodiment relates to a system for harvesting insects, the system including a tank for holding or growing insects or both; a negative stimulus device for moving live insects toward a direction or point; and a positive stimulus device for attracting live insects toward a second direction or point, wherein the system separates healthy or mobile insects from less healthy or mobile insects. The system may also include: a one-way valve or device that inhibits an insect from returning to the tank, a slide or device that directs an insect toward a destination; wherein the first direction or point is the same as the second direction or point. a camera for observing insects, a (video) camera for counting insects, a computer for recording data, a destination box for capturing live insects; a sensor or scale for counting, weighing or quantifying live insects in a destination box; wherein the destination box is a product box, or the negative stimulus device creating one or more of the following: light, sound, vibration.

DETAILED DESCRIPTION

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

Embodiments herein relate to systems, apparatuses, and methods for farming insects. Insect farming allows the development of high-quality protein sources for human or animal consumption in an eco-friendly manner. Insects that may be farmed include crickets, grasshoppers, flies, mealworms, ants, and so on. Embodiments herein may be used to farm any of the aforementioned insects, and, in particular, may be used for cricket farming.

Washable Insect Harborage

Figure 1:
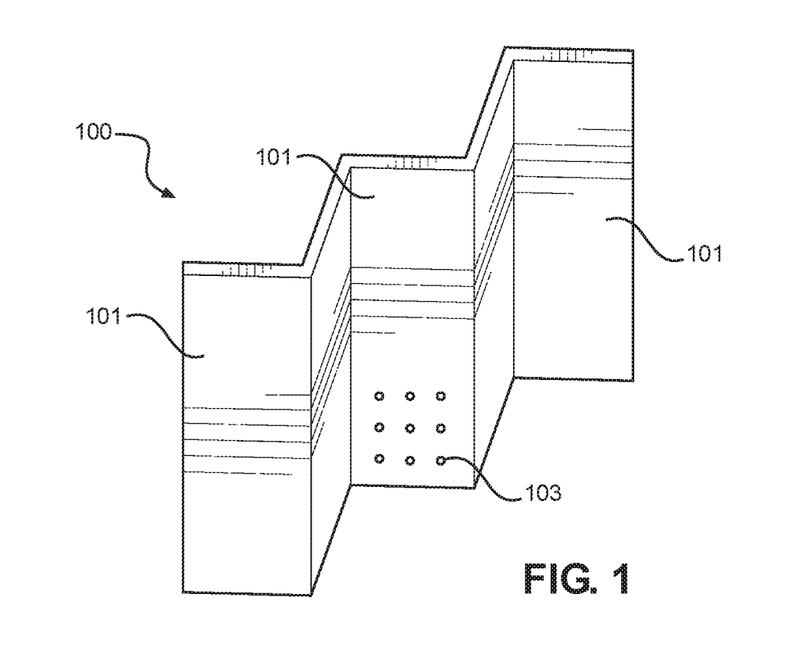
FIG. 1 illustrates an exemplary reusable harborage design.

FIG. 1 illustrates an exemplary harborage 100 for insects, such as, but not limited to crickets. Harborages are used in insect rearing tanks and provide a living quarters for the insects where the insects may hide, walk on and around, and so forth. The harborage may have a plurality of sides 101 that may be made of non-absorptive plastic. The harborage may have an irregular, slightly rough surface such as with bumps, grooves, crevices, and niches (each 103). The non-absorptive plastic may prevent the propagation of disease and protect future generations of insects from viruses, bacteria, and mold from previous generations as the non-absorptive nature of the plastic reduces the adherence of viruses, bacteria, and mold as compared to paper fiber harborages. Moreover, the plastic harborages may be cleaned in order to disinfect it prior to reuse. The harborage may have a high surface area per volume to allow a larger quantity of insects to attach or hang on to the harborage. Moreover, the geometry of the harborage may be designed for easy navigation by the insects. Insects may hang on to the vertical surface area of the harborage. The harborage may have a geometry configured to allow shaking of insects from the harborage. The harborage may have a geometry configured to allow fecal matter, exoskeletons, and dead insects to fall to the floor of the rearing tank, which may keep this biomatter away from living insects. Thus, to easily remove insects from a rearing tank, a human worker may remove the harborage and shake off the insects. FIG. 1 illustrates a harborage having a zig-zag pattern, but other geometries are also contemplated.

It may be desirable for insect farmers to see the insects but allow the insects privacy by giving the insects the impression that they are hidden. In one embodiment, the harborage may be constructed of a translucent or transparent red material. The translucent or transparent material may allow insect farmers to observe the insects. Some insects do not see the color red and therefore cannot see through the material, giving them the impression that they are hidden. The color of the transparent harborage may be selected to account for the spectrum visible to the insect. Colors other than red that are not visible to the insects may be chosen.

Figure 2:
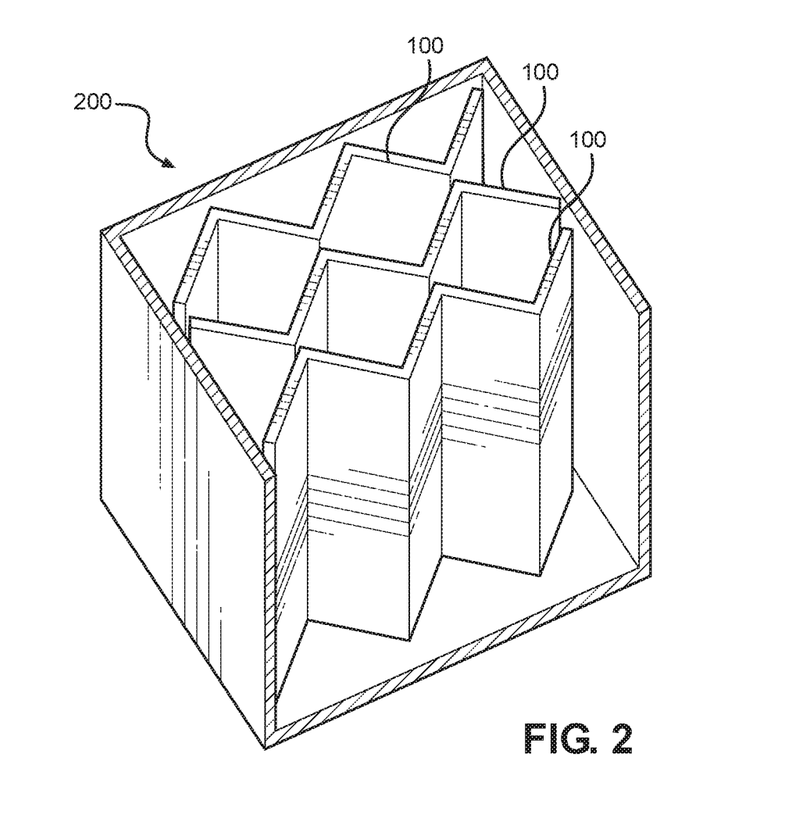
FIG. 2 illustrates multiple exemplary harborages situated in a rearing tank for insects.

FIG. 2 illustrates multiple exemplary harborages 100 situated in a rearing tank 200 for insects. The harborages may comprise one or more connectors for connecting to other harborages, such that the connected harborages occupy an entire insect rearing tank. This configuration may allow human workers to shake off all insects within a single rearing tank at once and may save the workers time and increase efficiency. In one motion, a human worker may grab one of the harborages and pull the harborage out of the tank. Because the other harborages are connected, the other harborages will also be lifted out of the tank. The human worker may then shake the plurality of connected harborages to remove the insects from the harborage and place them in another container, such as a transportation container.

Automated Water of Insects and Ozone Disinfection of Insect Drinking Water

Figure 3:
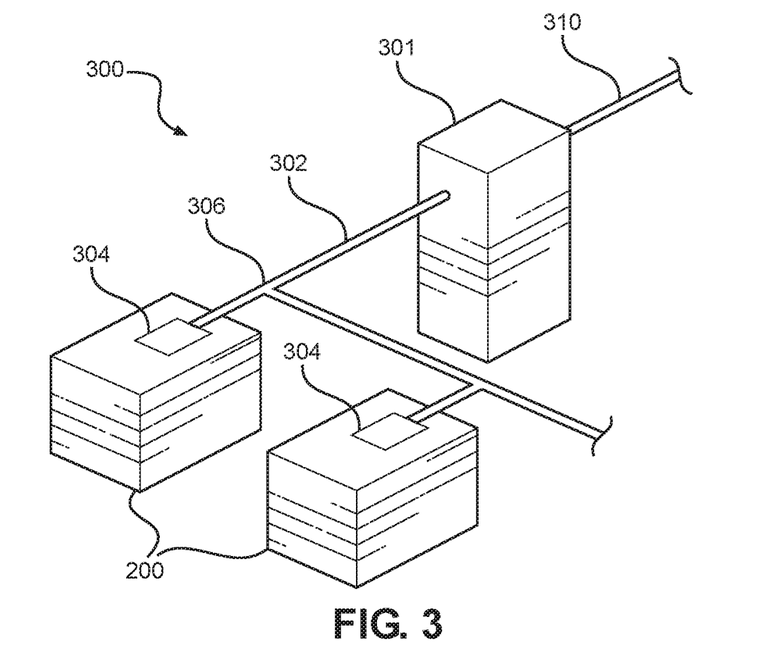
FIG. 3 illustrates an exemplary system for ozonating water for presentation to reared insects.

FIG. 3 illustrates an exemplary system 300 for ozonating water (infusing water with ozone) water for presentation to reared insects, such as, but not limited to crickets. The system may comprise an ozonate 301 for infusing water with ozone. Pressurized water is passed through the ozonator through a water inlet 310. The ozonated water has antimicrobial properties that may reduce the spread of diseases via bio-contaminants. The ozonator 301 is connected via a tube 302 to one or more insect tanks 200 containing insects. In each of the insect tanks, there may be one or more water presentation devices 304 that may comprise sponges, dishes, or mesh covered dishes, where each water presentation device may receive ozonated water. In the case of mesh covered dishes, the mesh may be present to prevent the insects from drowning in the water dish. If the insects do not consume enough water for any reason, water may stagnate in the water presentation devices 304. Stagnated water may become denatured and lose its antimicrobial properties.

Figure 4:
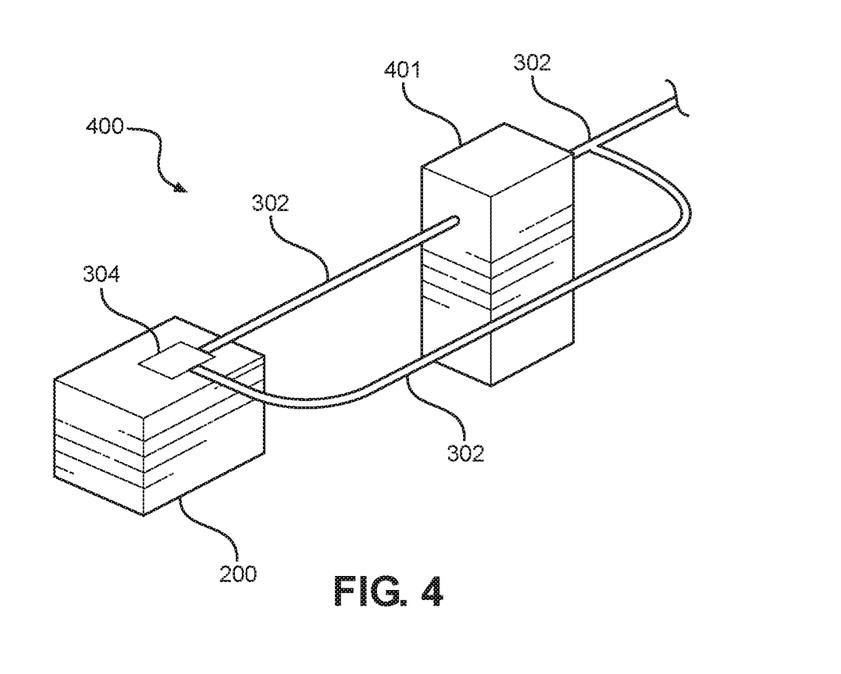
FIG. 4 illustrates an exemplary recirculating system for presentation of water to reared insects.

Therefore, as shown in FIG. 4, the system may also contain a recirculating system 400 with a recirculator 401 that draws water from the one or more water presentation devices 304, infuses the water with ozone, and recirculates the water to the water presentation devices 304 on the tanks 200. Due to the recirculation, water may be conserved. If the ozonated water contains bio-contaminants like feces, it may not harbor as many pathogens, bacteria, or fungi as non-ozonated water. This may improve the health of the insects and reduce the need to replace or clean the watering device. The system may have one or more valves 306 to control the flow of water, and the valves may be automatically controlled by computer to open or close based upon environmental conditions, weather, time, etc.

Alternatively, rather than using a single ozonator to ozonate the water for multiple insect tanks, an ozonator may be situated in each individual insect tank to ozonate the water provided to the insects in the single insect tank. The single ozonator may receive pressurized water from a first tube and infuse the water with ozone. A second tube may connect the pressurized ozonated water to a water presentation device in the insect tank.

An embodiment of automated watering system of insects, such as, but not limited to crickets, may include components such as a water source, water pump, tubing, valves, and so on. Such a system may reduce insect farm worker labor, increase reliability in watering, and provide farm operations with knowledge of water consumption in different insect rearing tanks.

In one embodiment, there may be a series of tubes connected to a water source via a pump. There may be a series of tubes that connect to one or more insect rearing tanks. The tubes may also be connected to valves that may be actuated based on humidity, float, or other sensor. In some embodiments, variable flow valves are used. In other embodiments, on/off valves are used.

In another embodiment, the series of tubes may have a precise flow rate perpetually allowing the flow of water at the approximate average rate that water is removed from the system. The valves may be opened periodically and briefly to replenish the water reservoir or absorptive material.

Another embodiment may further comprise a trench or trough allowing water to be supplied into or underneath an insect tank. One embodiment further comprises an absorptive material protects the insects from drowning and still allows them to access water from the water inside the tube or trough. Another embodiment further comprises a plate that protects the insects from falling into the water and drowning but allows them to access the water level just above the plate. Another embodiment further comprises a grate or mesh allows the insect's face to reach the water but prevents their bodies from falling in. See also FIG. 11.

Another embodiment may further comprise a recirculating device for recirculating water from the water presentation devices in the one or more insect tanks. In one embodiment, a passive mechanical material property may be used to regulate the humidity of the absorptive material or the height of water in the reservoir. In another embodiment, the recirculating device may present a face of flowing water to the insects.

Insect Antiviral and Antibiotic

Zoonotic diseases may decimate entire populations of insects in a farming operation. It may then be desirable to prevent diseases from spreading in insect farming operations. Successfully preventing disease spread may allow insect farmers to save their current stock and continue to use their current farm without incurring additional costs to restart insect populations, losing bred stock, or relocating the insect farm.

An exemplary method for treating a population of farmed insects, such as, but not limited to crickets, for preventing disease may include the following steps. Upon discovery of a bacterial or viral infection in the farmed insect population, the zoonotic infection in a population of farmed insects is identified. The diagnosis of the infection may be performed by examining one or more live insects or one or more dead insects. Next, an antiviral or antibiotic effective to treat the identified zoonotic infection is identified. Such an antiviral or antibiotic may include Virkon, Aciclovir, penicillins, cephalosporins, macrolides, fluoroquinolones, sulfonamides, tetracyclines, aminoglycosides, and other compounds. Next, the identified antiviral or antibiotic is administered to the population of farmed insects. Administration of the antiviral or antibiotic to the insects may be performed by feeding, injection, spraying, dusting, or other methods of administration. In one embodiment, administration of antiviral or antibiotic is prophylactic so as to prevent the development of the zoonotic disease.

Figures 5, 6:
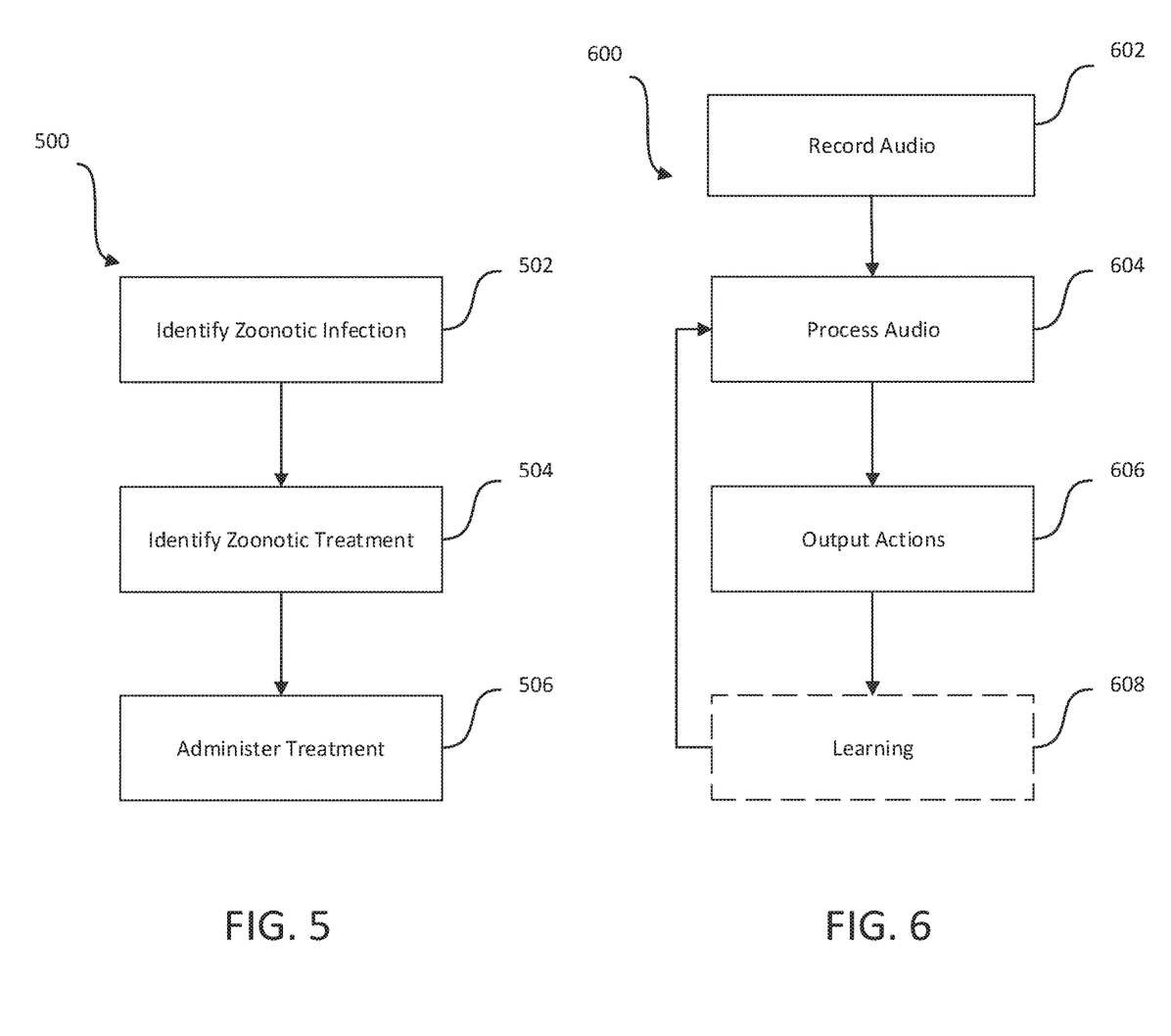
FIG. 5 illustrates an exemplary method for treating insects for disease.
FIG. 6 illustrates an exemplary method for audio processing of insect chirps.

As illustrated in the flow chart of FIG. 5, the above method 500 may be practiced as such. The zoonotic infection in a population of farmed insects is identified 502. Next, an antiviral or antibiotic effective to treat the identified zoonotic infection is identified 504. Next, the identified antiviral or antibiotic is administered to the population of farmed insects 506.

Chirp Processing

One embodiment of a chirp processing system may detect auditory cues from insects, such as, but not limited to crickets, to learn about insect state and inform choice of a farming action or farm action time. A farm action is an action performed in the insect farming process, and a farm action time is a time for performing a farm action. Some embodiments may detect finer and more complex changes in insects than the human ear. The system may also adapt to changing environmental conditions like temperature and nutrition better than farm operators and account for factors affecting insect maturation. The system may make standardized and optimal decisions for farm activities like when to harvest or collect insect eggs.

Embodiments of the invention may allow untrained and new insect farmers to have optimal timings of farm activities without spending years listening to insects and deciphering the meanings of different sounds. Embodiments may allow insect farmers to compare timings of farm activities against a prescribed program and to better discuss the timings with other insect farmers. Embodiments may allow machine learning and other computer tools to better inform farm operation processes and improve them over time.

An exemplary method for processing for processing chirp information from insects to determine farm action times may have the following steps. As illustrated in the flow chart of FIG. 6, the above method 600 may be practiced as such. First, audio information comprising insect chirps may be recorded by a microphone 602. Next, the audio information comprising insect chirps may be processed 604. Next, farm action times are determined based on the audio information comprising insect chirps 606. Training of a learning system to perform farm actions may be incorporated 608 into the method 600.

This method is useful because insects have their exoskeletons on the outside, which makes it very difficult for insect farmers to assess health characteristics of individuals in their colonies. This gives behavioral markers an increased importance in insect farming compared to the farming of vertebrates, which can be diagnosed for health by the color of their tongue, plaque on their teeth, clouding of eyes, quality pelt, etc.

Crickets make songs generally with a (1) toothed file member, and a (2) plucking member called a plectrum. By raking the plectrum through the teeth of the combed file they can produce different numbers of pulses at different frequencies and volumes. They can pattern these sounds, called chirps or trills, together into different songs. Most species have at least three distinct songs: calling (drawing a mate in), courtship, and an aggressive song usually used against competing mates. The aggressive song can be identified because it generally has more of the first type of chirp, causing more pulses per chirp. Note that with the second sounds, a louder and more forceful raking causes a louder sound and the frequency is slower and the trill duration longer due to the higher force applied to the plectrum. Cricket song qualities are generally inherited, and improvisations exist. The heritability of songs means songs could signal moments after a genetic bottle-necking and improvisation could be a marker for superior mental health or other population dynamics such as increased memetic competition.

From song characteristics such as number of chirps from a bin, chirp duration, chirp periodicity, frequency, and number of pulses per chirp, one can deduce things such as the relative number of mate ready adults, the level of mate competition and aggressive behavior exhibited. These qualities can inform farmers about the size and health of the cricket colony or inform actions such as inserting egg laying medium when there are a peak number of mating adults, or dividing a colony into two colonies to decrease density and reduce aggressive mating behavior. Industrial equipment sounds can scare colonies into a stressed state where mating behavior and the chirping associated with it decreases or ceases completely. Monitoring and reducing such stress can increase yields on a farm.

The overall volume of the whole colony will generally increase as the mating adults mature. Juvenile crickets do not chirp. It takes roughly a week after the first chirps start to have a fertile population ready to lay because they need time to mate. Computer recording and analysis aids monitoring of the onset of chirps, because the spread in maturity the crickets in the colony could be on the order of days or weeks and can be difficult to ascertain by human judgement alone. A few adults chirping is not the right time to harvest, and when the volume starts decreasing it's generally too late to get optimal yields.

Louder bins correlate with more mature crickets and also more eggs creation (both more crickets and healthier and louder crickets mean more eggs). One can AB test and optimize nutrition and other environmental effects around sound analysis easier than counting eggs, and one can predict the size of the next generation a few weeks earlier than by egg counting. Cricket temperature is correlated to the periodicity of the chirps and is a useful metric, since metabolism, metabolism, and food consumption are also correlated.

Figure 7:
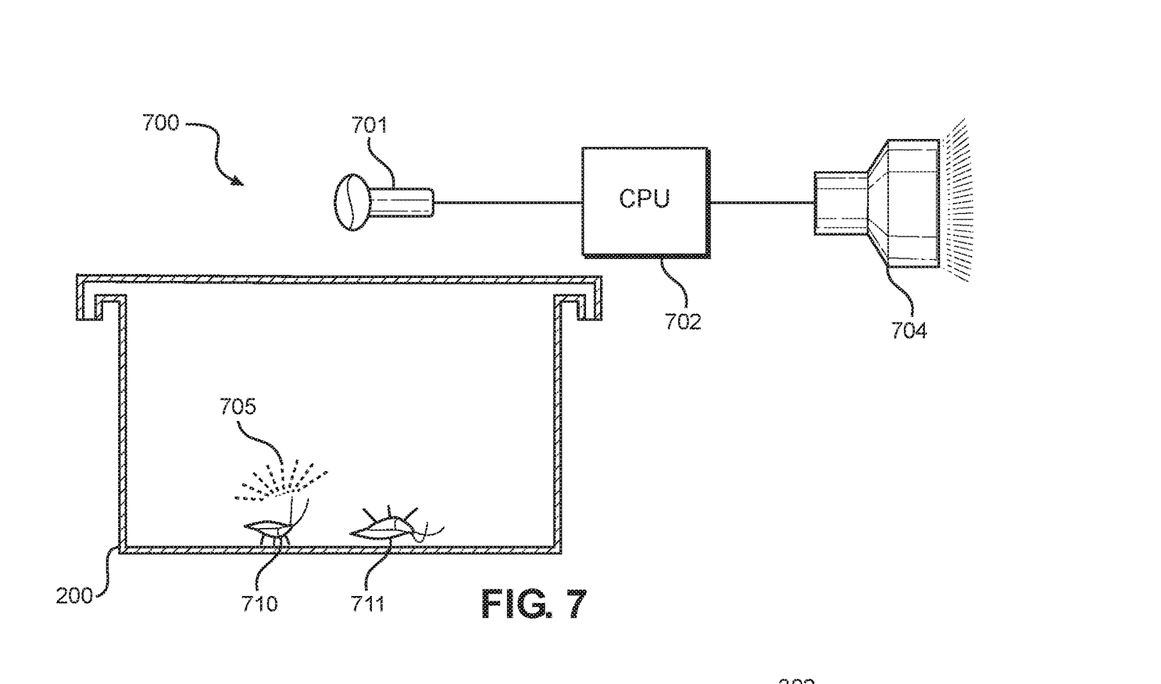
FIG. 7 illustrates an exemplary system for detecting and processing auditory information from an insect rearing tank.

FIG. 7 illustrates an exemplary system 700 for detecting and processing auditory information 705 from insects from an insect rearing tank. A microphone or other audio sensor 701 is positioned near an insect rearing tank 200. Rearing tank 200 may be one or more rearing tanks and microphone or other audio sensor 701 may be one or multiple devices. The audio signal is transmitted wired or wirelessly to computer system 702. The computer system 702 may process the audio information and determine farm action times. Computer system 702 may then send information or instructions, such as to actuate one or more insect farming systems or devices, such as a watering system, through interface 704. A schematic live insect 710 and dead insect 711 are also shown.

Based on the processing of audio information comprising insect chirps, a computer system may determine that certain farm actions are appropriate such as presentation of an ovaposition medium, removal of an ovaposition medium, moving insects into more or fewer tanks of the same or different size, altering the feed composition of the insects as they grow, changing presentation devices for food and water, determining optimal time to harvest, and other farm actions.

One embodiment may determine insect sexual maturity based on the audio information comprising insect chirps and determine an action time for placing an ovaposition medium, such as egg trays, in an insect tank to allow the insects to lay eggs. Auditory cues from the insects may be mating calls that the computer system may detect. By processing the auditory cues to determine that the auditory cues are mating calls, the computer system may present a notification that a farm action should be taken based on the sexual maturity level of the insects, such as placing an ovaposition medium.

One embodiment may determine insect maturity based on the audio information comprising insect chirps and determine an action time for removing an ovaposition medium.

One embodiment may determine insect maturity based on the audio information comprising insect chirps and determine an action time for moving insects into a different tank, which may be the same size or a different size than the current tank.

One embodiment may determine insect maturity based on the audio information comprising insect chirps and determine an action time for moving insects into a different tank, which may be the same size or a different size than the current tank.

One embodiment may determine insect maturity based on the audio information comprising insect chirps and determine an action time for changing a water presentation device or food presentation device for presenting food or water to the insects.

One embodiment may determine insect maturity based on the audio information comprising insect chirps and determine an action time for changing the nutrition of one or more insects based on the insect maturity.

Another embodiment may determine insect maturity based on the audio information comprising insect chirps and determine an action time for harvesting one or more insects based on the insect maturity.

Another embodiment may determine insect health based on the audio information comprising insect chirps.

Another embodiment may determine insect maturity based on the audio information comprising insect chirps and determine an action time for changing the watering policy for one or more insects based on the insect maturity.

One embodiment may record, by a microphone, audio information comprising insect chirps from a plurality of insect rearing tanks.

Another embodiment may record, by a microphone, audio information comprising insect chirps from a single insect rearing tank.

Another embodiment may record and process the audio information by a single microphone and single computer system.

Another embodiment may record and process the audio information by a plurality of microphones and a plurality of computer systems.

Another embodiment may receive additional sensor information, process the additional sensor information, and combine the additional sensor information with the audio information comprising insect chirps to determine farm action times.

Another embodiment may use final yield data of harvested insects to train a learning system to perform farm actions based on audio information comprising insect chirps to improve final yield.

Ceiling Sponge

It may be desirable in insect farming operations to prevent the spread of pathogens, fungus, and viruses while also decreasing the labor in tending to the watering systems. Embodiments of this invention may allow gravity to safely remove biomatter such as feces, thereby reducing the spread of disease in insect watering systems.

Figure 8:
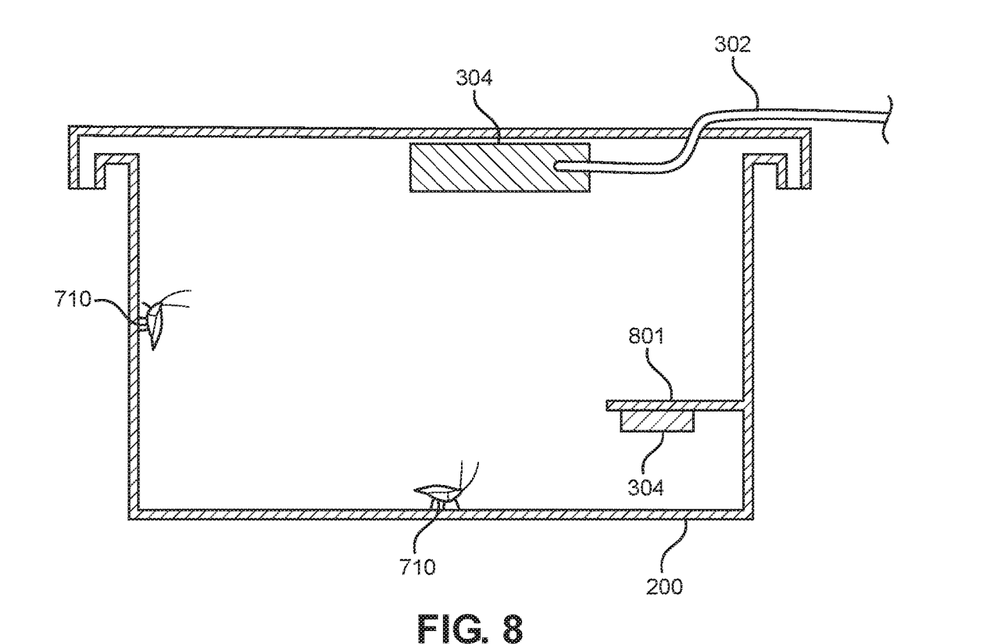
FIG. 8 illustrates exemplary systems for supplying water to insects via an absorptive watering device.

FIG. 8 illustrates exemplary systems for supplying water to insects such as, but not limited to crickets, via an absorptive watering device. Insect rearing tank 200 holds the harborages for farmed insects in an insect farming operation. Rearing tank 200 may contain one or more of absorptive watering devices 304. The absorptive water device may be made of an absorptive material and may be, for example, a sponge or a gel. The absorptive water device 304 may be positioned on a tilted mount 801 in an insect rearing tank. Alternatively, the absorptive watering device may be positioned on a wall of an insect rearing tank. Alternatively, the absorptive watering device may be positioned on the ceiling of an insect rearing tank. Alternatively, the absorptive water device may be positioned an overhang of an insect rearing tank.

In each of the embodiments of an absorptive watering device, the absorptive water device is positioned in rearing tank 200 such that gravity prevents feces and other biocontaminants from remaining on the absorptive watering device. This may have the effect of limiting and decreasing biocontamination and the spread of pathogens, fungus, and viruses inside of an insect farming operation, while reducing the labor of keeping absorptive watering devices clean. Most insects may still climb on to and drink from an absorptive watering device positioned in such a way.

Counted and Measured Egg Pods for Insect Farming

In insect farming operations, it may be desirable to have accurate accounting of the number of insects, in a rearing tank, packaging box, or other container. This information may help farming operations direct the farm activities and make business decisions.

One embodiment of a system to provide counted and measured egg pods for insect farming comprises a container including a counted number of insect eggs, which may be, for example, cricket eggs. The container may contain a wet absorptive material on which a counted number of insect eggs of predefined quantity rest. The wet material may keep the insect eggs moist, which is desirable to maintain the eggs' viability. The structure of the container may be designed to prevent the insect eggs from being crushed or otherwise damaged in transit and to retain moisture in the insect eggs' environment. The predefined quantity may be determined by calculating the number of eggs required to achieve a desired yield rate based on an expected hatch rate. The container size and number of eggs contained therein may be designed specifically for the size of the target insect rearing tank in which the eggs will hatch. There may exist multiple predefined sizes for variously sized target rearing tanks.

In some embodiments, the counted number of insect eggs is a predefined exact number. Alternatively, there may be a natural tolerance of a few percent such as 1%.

One embodiment allows insect farming operations to ship counted numbers of eggs safely to other insect farming operations, eliminating the need for individual farmers to measure live baby insects, which is a labor-intensive practice with high mortality rate for the insects.

Embodiments may allow the entire egg shipping container to be placed in the insect habitat and allowed to hatch with minimal farm worker intervention and supervision.

Figure 9:
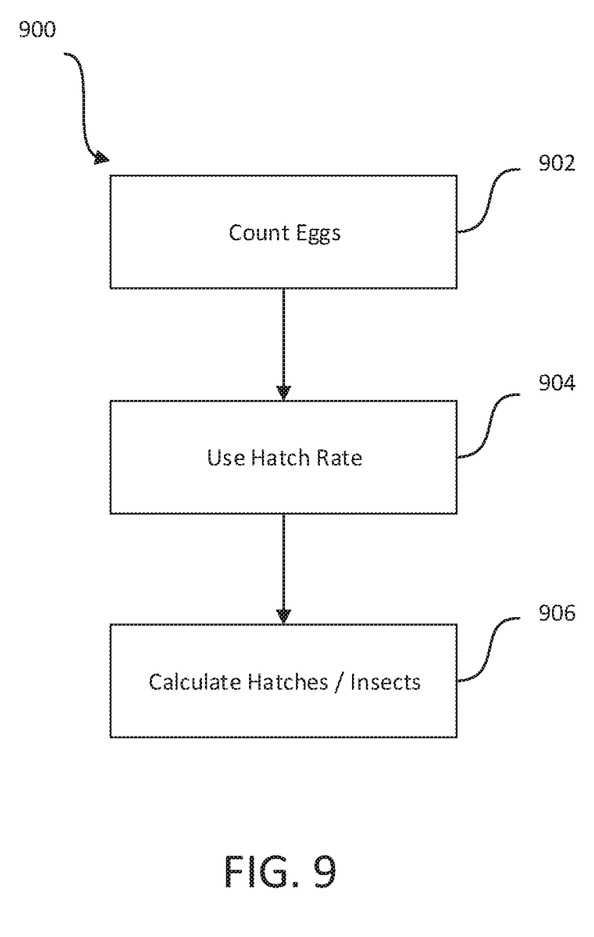
FIG. 9 illustrates an exemplary method for predicting insect hatching.

As illustrated in the flow chart of FIG. 9, the above method 900 may be practiced as such. First, count the eggs in a particular defined section or area 902. Next, obtain or estimate a useful hatch rate 604. Next, calculate an expected number of hatches or insects 906.

Automated Insect Harvester

In insect farming operations, it may often be advantageous to have automated harvesting of insects. Doing so may allow farming operations to easily scale their farming operations while reducing labor and increasing the speed of harvest.

In one embodiment of an automated harvesting system for harvesting insects, such as, but not limited to crickets, a first container including one or more live insects and one or more dead insects is connected to a second container. Live insects are encouraged through a stimulus to travel in the direction of a one-way passage where the one-way passage may lead from the first container to a second container and where the one-way passage allows traversal in only a single direction. Optionally, the harvester may have a computer-enabled mechanism for counting insects traversing the one-way passage. Counting insects by the harvester is an optional component and is not required.

In another embodiment of an automated harvesting system for harvesting insects, a first container including one or more live insects and one or more dead insects is connected to a second container. Live insects are encouraged through a stimulus to travel in the direction of a one-way passage where the one-way passage may lead from the first container to a second container and where the one-way passage allows traversal in only a single direction. Optionally, a camera may be angled to record insects traversing the one-way passage. A computer system, communicatively connected to the camera, comprising a non-transitory computer-readable medium including instructions implementing a computer vision system for counting insects may exist and for identifying when all living insects have been collected.

In one embodiment, counting insects may be performed by a camera system and computer system performing image recognition (when referred to herein camera may also be a video camera). In another embodiment, counting may be performed by using small turnstile like sensors along the insects' path from a first container to the second container. In another embodiment, there may exist a cliff or slide that allows the use of a camera connected to a computer system. The computer system may use machine vision techniques to count the insects. These two embodiments may be used together or separately. Camera verification and camera-based counting may be useful in many embodiments. A scale may optionally be placed under the second container to record the total weight of all insects in the container.

When the second container is filled, it may be replaced with another container either by a farm worker or by automation such as a conveyor belt.

Figure 10:
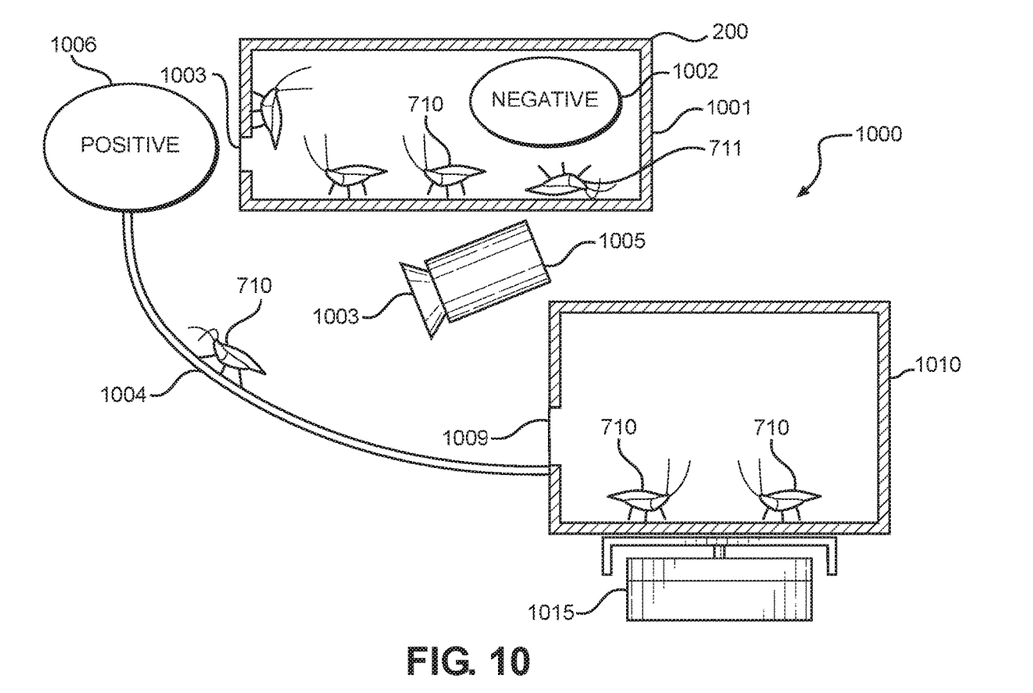
FIG. 10 illustrates an exemplary system for an automated insect harvester.

FIG. 10 illustrates an exemplary system for an automated insect harvester. Harvest tank 200 holds insects awaiting packaging. Harvest tank 200 may contain some negative insect stimulus 702 that may cause live insects to leave the tank through opening 1003 and optionally onto a one-way slide 1004 (one-way largely due to gravity). There may be a positive insect stimulus 1006 outside of opening 1003 to encourage live insects to leave harvest tank 200. Depending on type of insect, negative and positive stimuli may include one or more of the following: heat, light, vibration, pheromones, brush or panel mechanisms. The stimuli may be used individually, in sequence, or in other combinations. Opening 1003 is connected to product box 1010 by counting slide 1004. The product box can generally be delivered straight to consumers. As the insects 510 traverse counting slide 704, a camera 1005 can capture their movement, and the camera can be connected to a computer via a network, Internet, etc., to process insect data. When the insects reach opening 1009 of packaging box 1010, the insects will enter the packaging box 1010. Weight scale 1015 will measure the total weight of accumulated insects in packaging box 1010. Input from camera 1005, scale 1015, and any sensors on counting slide 1004 may then be fed to a computer system to perform calculations to count the total number of insects in packaging box 1010.

Figure 11:
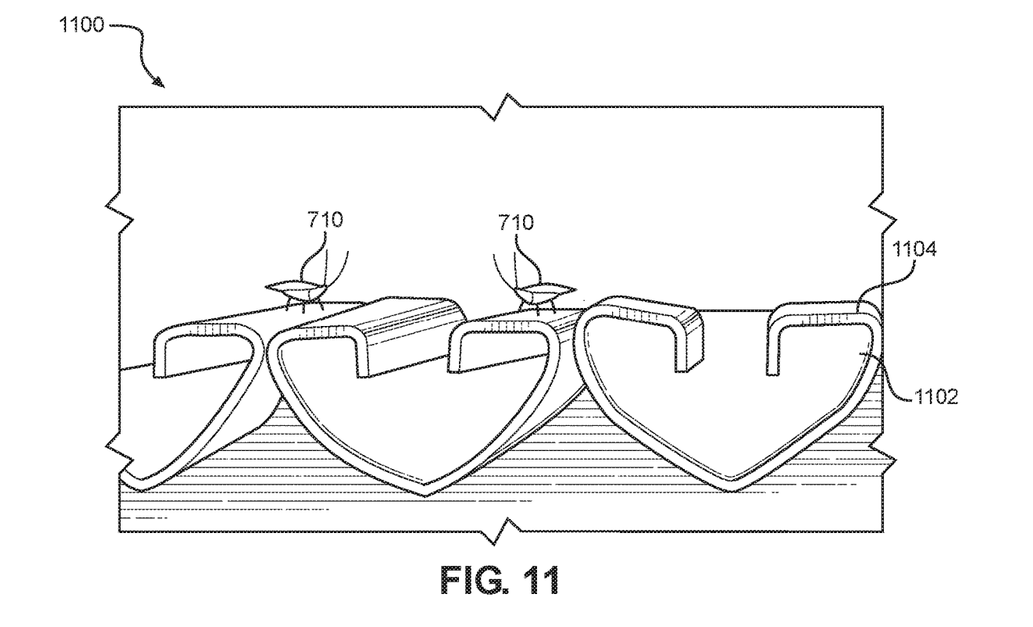
FIG. 11 illustrates a flow trench or trough.

FIG. 11 illustrates a flow trench or trough 1100, typically made of plastic, metal, etc., allowing water to be supplied into or underneath an insect tank. Water is supplied via the inside 1102 of the trench. Insects 710 can stand on top of the trench on a platform 1104 so they can access water with drowning. In an alternative embodiment, part or all of a platform can have or can be a water presentation device such as a sponge, thus allowing the insect to access water without being in the trench. In an alternative embodiment, part or all of a platform can have or can be a mesh grate wherein water can flow over the mesh grate, thus allowing the insect to access water without being in the trench. In an alternative embodiment, part or all of a platform can have or can be a type of plate with holes or openings, wherein water can flow over the plate but still fall into the trench, without being in the trench, thus allowing the insect to access water without being in the trench.

Figure 12:
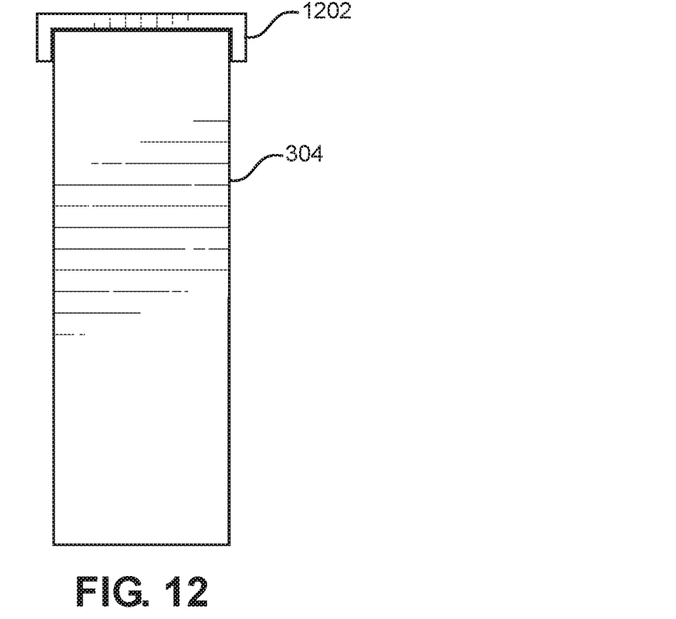
FIG. 12 illustrates an embodiment of a water presentation device sponge with a cap.

FIG. 12 illustrates an embodiment of a water presentation device 304 such as a sponge with a cap 1202 to prevent debris an contaminants from getting on the sponge and/or contaminating the water.

Figure 13:
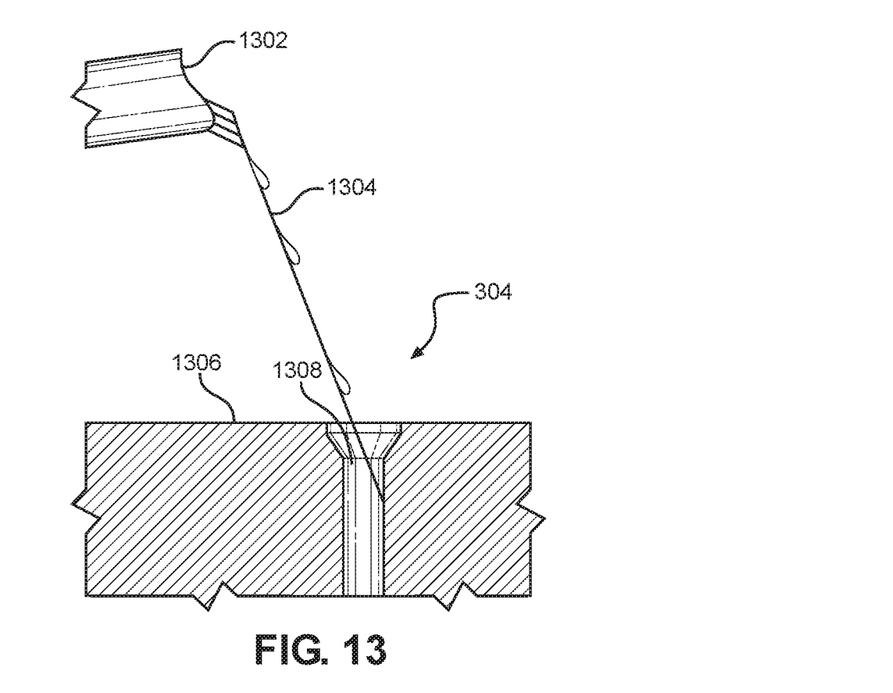
FIG. 13 illustrates another embodiment of a water presentation device.

FIG. 13 illustrates an embodiment of a water presentation device 304 that includes a string or other wettable material 1304 than can be strung between an origin and insertion. Typically there is a water source 1302 that wets the material 1304 and a drain 1308 for excess water. The device 304 is shown in the context of a floor 1306 of an insect tank.

Terminology

The terminology used herein is for the purpose of describing particular aspects only and is not intended to be limiting of the disclosure. As used herein, the singular forms "a," "an," and "the" are intended to comprise the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

While various embodiments constructed according to the principles disclosed herein, as well as specific components, have been described above, it should be understood that they have been presented by way of example only, and not limitation. Thus, the breadth and scope of the invention should not be limited by any of the above-described exemplary embodiments, but should be defined only in accordance with the following claims and their equivalents.

Computer Implementations

Embodiments of the invention may comprise one or more computers. Embodiments of the invention may comprise software and/or hardware. Some embodiments of the invention may be software only and may reside on hardware. A computer may be special-purpose or general purpose. A computer or computer system includes without limitation electronic devices performing computations on a processor or CPU, personal computers, desktop computers, laptop computers, mobile devices, cellular phones, smart phones, PDAs, pagers, multi-processor-based devices, microprocessor-based devices, programmable consumer electronics, cloud computers, tablets, minicomputers, mainframe computers, server computers, microcontroller-based devices, DSP-based devices, embedded computers, wearable computers, electronic glasses, computerized watches, and the like. A computer or computer system further includes distributed systems, which are systems of multiple computers (of any of the aforementioned kinds) that interact with each other, possibly over a network. Distributed systems may include clusters, grids, shared memory systems, message passing systems, and so forth. Thus, embodiments of the invention may be practiced in distributed environments involving local and remote computer systems. In a distributed system, aspects of the invention may reside on multiple computer systems.

Embodiments of the invention may comprise computer-readable media having computer-executable instructions or data stored thereon. A computer-readable media is physical media that can be accessed by a computer. It may be non-transitory. Examples of computer-readable media include, but are not limited to, RAM, ROM, hard disks, flash memory, DVDs, CDs, magnetic tape, and floppy disks.

Computer-executable instructions comprise, for example, instructions which cause a computer to perform a function or group of functions. Some instructions may include data. Computer executable instructions may be binaries, object code, intermediate format instructions such as assembly language, source code, byte code, scripts, and the like. Instructions may be stored in memory, where they may be accessed by a processor. A computer program is software that comprises multiple computer executable instructions.

A database is a collection of data and/or computer hardware used to store a collection of data. It includes databases, networks of databases, and other kinds of file storage, such as file systems. No particular kind of database must be used. The term database encompasses many kinds of databases such as hierarchical databases, relational databases, post-relational databases, object databases, graph databases, flat files, spreadsheets, tables, trees, and any other kind of database, collection of data, or storage for a collection of data.

A network comprises one or more data links that enable the transport of electronic data. Networks can connect computer systems. The term network includes local area network (LAN), wide area network (WAN), telephone networks, wireless networks, intranets, the Internet, and combinations of networks.

In this patent, the term "transmit" includes indirect as well as direct transmission. A computer X may transmit a message to computer Y through a network pathway including computer Z. Similarly, the term "send" includes indirect as well as direct sending. A computer X may send a message to computer Y through a network pathway including computer Z. Furthermore, the term "receive" includes receiving indirectly (e.g., through another party) as well as directly. A computer X may receive a message from computer Y through a network pathway including computer Z.

Similarly, the terms "connected to" and "coupled to" include indirect connection and indirect coupling in addition to direct connection and direct coupling. These terms include connection or coupling through a network pathway where the network pathway includes multiple elements.

To perform an action "based on" certain data or to make a decision "based on" certain data does not preclude that the action or decision may also be based on additional data as well. For example, a computer performs an action or makes a decision "based on" X, when the computer takes into account X in its action or decision, but the action or decision can also be based on Y.

In this patent, "computer program" means one or more computer programs. A person having ordinary skill in the art would recognize that single programs could be rewritten as multiple computer programs. Also, in this patent, "computer programs" should be interpreted to also include a single computer program. A person having ordinary skill in the art would recognize that multiple computer programs could be rewritten as a single computer program.

The term computer includes one or more computers. The term computer system includes one or more computer systems. The term computer server includes one or more computer servers. The term computer-readable medium includes one or more computer-readable media. The term database includes one or more databases.

The invention claimed is:

1. A system for harvesting insects, the system comprising:
a first tank for holding and growing live insects, the first tank having a first opening on a first side portion of the first tank, the first opening positioned higher than a bottom portion of the first tank;
a processing unit configured for:
receiving, from one or more microphones, auditory information from the live insects, wherein the auditory information comprises a plurality of chirps;
analyzing, by a chirp processing system, the received auditory information;
determining one or more activities to be performed based on the analysis; and sending, to an automated harvesting system, instructions to begin harvesting the live insects;

the automated harvesting system comprising:
- a negative stimulus device positioned within the first tank and proximate to a second side portion of the first tank, wherein the second side portion of the first tank is opposite to that of the first side portion;
- wherein the negative stimulus device is configured to expose the live insects to one or more first stimuli, and wherein the one or more first stimuli repel the live insects from the negative stimuli device and the second side portion of the first tank and towards the first opening on the first side portion of the first tank;
- a positive stimulus device positioned external to the first tank and proximate to the first opening, wherein the positive stimulus device is configured to attract the live insects through the first opening;
- a product box, positioned on a scale in communication with the processing unit, for receiving the live insects, the product box having a second opening for receiving the live insects;
- a slide positioned at the first opening of the first tank and coupled with the second opening of the product box, wherein the first opening of the first tank is positioned higher than the second opening of the product box;
- the slide configured to separate the live insects from dead insects by gravity transferring the live insects leaving the first tank through the first opening into the product box through the second opening; and
- a camera, in communication with the processing unit, oriented to capture one or more images of the live insects during gravity transfer;

wherein the processing unit is further configured to:
- receive the one or more captured images from the camera and a weight measurement of the product box from the scale;
- determine how many of the live insects have been transferred into the product box based on the one or more captured images and the weight of the product box after the live insects have been transferred; and
- calculating a final yield of harvested insects.

2. The system of claim 1 wherein the slide is further configured to inhibit a respective live insect from returning to the tank.

3. The system of claim 1 wherein the system is further configured for recording data on insect movement or behavior.

4. The system of claim 1 wherein the product box for capturing one or more of the live insects is a box suitable for delivery to consumers.

5. The system of claim 1 wherein the negative stimulus device creates one or more of the following: light, sound and vibration.

6. The system of claim 1 wherein analyzing the received auditory information further comprises identifying one or more song characteristics wherein the one or more song characteristics comprises a plurality of:
- number of chirps;
- chirp duration;
- chirp periodicity;
- chirp frequency; and
- number of pulses per chirp.

7. The system of claim 6 wherein analyzing the received auditory information further comprises determining one or more characteristics of the live insects based on the identified song characteristics.

8. The system of claim 7 wherein the determined one or more characteristics of the live insects comprises:
- relative number of mate ready adults;
- level of mate competition;
- level of aggressive behavior exhibited; and
- health of the live insects.

9. The system of claim 8 wherein, based on the one or more determined characteristics of the live insects, one or more activities to be performed are determined, wherein the one or more activities comprise:
- inserting egg laying medium;
- removing the egg laying medium;
- moving the live insects into more or fewer tanks;
- altering feed composition of the live insects;
- changing of food or water; and
- harvesting the live insects.

10. The system of claim 9 wherein, the chirp processing system further comprises a learning system, the learning system trained on the received auditory information and the final yield of harvested insects.

* * * * *